United States Patent [19]

Raper et al.

[11] Patent Number: 5,416,197
[45] Date of Patent: May 16, 1995

[54] ANTIBODIES WHICH BIND HUMAN COLLAPSIN

[75] Inventors: Jonathan A. Raper, Wynnewood; Yuling Luo, Philadlephia, both of Pa.

[73] Assignee: Trustees of the University of Pennsylvania, Philadelphia, Pa.

[21] Appl. No.: 136,922

[22] Filed: Oct. 15, 1993

[51] Int. Cl.$^6$ .............................................. C07K 16/22
[52] U.S. Cl. .............................. 530/387.9; 530/387.1; 530/388.24; 530/389.1; 530/389.2
[58] Field of Search ............. 530/387.9, 388.24, 389.1, 530/389.2, 387.1; 424/85.8

[56] References Cited

PUBLICATIONS

Meier, T. et al., J. Neuroscience, 13(4): 1498–1510, Apr. 9, 1993.
Fan, J. et al., J. Cell Biol, 121(3): 867–878, May 1993.
Kobodkin, A. L. et al., Neuron, 9: 831–845, Nov. 1992.
Luo, Y. et al., Cell, 75: 217–227, Oct. 22, 1993.
Seirer, E. D. et al., Clin Chem, 27(11): 1797–1806, 1981.
Bandtlow et al., "Oligodendrocytes arrest neurite outgrowth by contact inhibition," J. Neurosci., 10:3837–3848, 1990.
Bandtlow et al., "Role of intracellular calcium in NI-3-5-evoked collapse of neuronal growth cones," Science, 259:80–83, 1993.
Bentley et al., "Disoriented pathfinding by pioneer neurone growth cones deprived of filopodia by cytochalasin treatment," Nature, 323:712–715, 1986.
Caroni et al., "Two membrane protein fractions from rat central myelin with inhibitory properties for neurite growth and fibroblast spreading," J. Cell. Biol., 106:1281–1288, 1988.
Caroni et al., "Antibody against myelin-associated inhibitor of neurite growth neutralizes nonpermissive substrate properties of white matter," Neuron, 1:85–96, 1988.
Chang et al., "Extension of neurites on axons is impaired by antibodies against specific neural cell surface glycoprotein," J. Cell. Biol., 104:355–362, 1987.
Cox et al., "Axonal guidance in the chick visual system: posterior tectal membranes induce collapse of growth cones frmo the temporal retina," Neuron., 2:31–37, 1990.
Davies et al., "Isolation from chick somites of a glycoprotein fraction that causes collapse of dorsal root ganglion cones," Neuron., 2:11–20, 1990.
Fawcett et al., "Oligodendrocytes repel axons and cause growth cone collapse," J. Cell. Sci., 92:93–100, 1989.
Harlow et al., Antibodies: A Laboratory Manual New York: Cold Spring Harbor, 1988.
Igarashi et al., "Mediation by G proteins of signals that cause collapse of growth cones," Science, 259:77–79, 1993.

(List continued on next page.)

Primary Examiner—David L. Lacey
Assistant Examiner—Susan A. Loring
Attorney, Agent, or Firm—Woodcock, Washburn, Kurtz, Mackiewicz & Norris

[57] ABSTRACT

Essentially pure human collapsin and its uses are disclosed. An isolated nucleic acid molecule that comprises a nucleotide sequence that is complementary to a nucleotide sequence that encodes a portion of human collapsin is disclosed. Antibodies that specifically bind to human collapsin and that inhibit its activity are disclosed. Methods of inhibiting the activity of collapsin, methods of inducing neurite outgrowth and methods of treating individuals suffering from nerve damage comprising the step of contacting neuronal cells with nucleic acid molecule that comprises a nucleotide sequence that is complementary to a nucleotide sequence that encodes a portion of human collapsin or comprising the step of contacting a neuronal cell with an antibody that specifically binds to human collapsin are disclosed. Methods of identifying compounds that inhibit the activity of human collapsin comprising the steps of contacting a neuronal cell with human collapsin in the presence of a test compound are disclosed.

3 Claims, No Drawings

OTHER PUBLICATIONS

Ivins et al., "Intracellular calcium levels do not change during contact-mediated collapse of chick DRG growth cone structure," *J. Neurosci.*, 11:1597–1608, 1991.

Kapfhammer et al., "Collapse of growth cone structure on contact with specific neurites in culture," *J. Neurosci.*, 7:201–212, 1987.

Kaphammer et al., "Interactions between growth cones and neurites growing from different neural tissues in culture," *J. Neurosci.*, 7:1595–1600, 1987.

Loose-Mitchell, "Antisense nucleic acids as a potential class of pharmaceutical agents," *TIPS*, 9:45–47, 1988.

Marcus-Sekura, Carol J., "Techniques for Using Antisense Oligodeoxyribonucleotides to Study Gene Expression," *Anal. Biochemistry*, 172:289–295, 1988.

Raper et al., "Temporal retinal growth cones collapse on contact with nasal retinal axons," *Exp. Neurol.*, 109:70–74, 1990.

Raper et al., "The enrichment of a neuronal growth cone collapsing activity from embryonic chick brain," *Neuron.*, 4:21–29, 1990.

Schnell et al., "Axonal regeneration in the rat spinal cord produced by an antibody against myelin-associated neurite growth inhibitors," *Nature*, 343:269–272, 1990.

Stein et al., "Oligodeoxynucleotides as Inhibitors of Gene Expression: A Review," *Cancer Research*, 48:2659–2668, 1988.

Tosney et al., "Pattern and specificity of axonal outgrowth following varying degrees of chick limb bud ablations," *J. Neurosci.*, 4:2518–2527, 1984.

Van der Krol, A. R., "Modulation of Eukaryotic Gene Expression by Complementary RNA or DNA Sequences, J. N. Mol, & A. R. Stuitje," *BioTechniques*, 6:958–973, 1988.

Walder, "Antisense DNA and RNA: progress and prospects," *Genes & Development*, 2:502–504, 1988.

Zon, G., "Synthesis of Backbone-Modified DNA Analogues for Biological Applications," *Journal of Protein Chemistry*, 6:131–145, 1987.

Zon, G., "Oligonucleotide Analogures ASD Potential Chemotherapeutics Agents," *Pharmaceutical Research*, 5:539–549, 1988.

ANTIBODIES WHICH BIND HUMAN COLLAPSIN

ACKNOWLEDGEMENT OF GOVERNMENT SUPPORT

This invention was made with Government support under National Institutes of Health grant R01NS26527. The Government has certain rights in this invention.

FIELD THE INVENTION

The present invention relates to compositions that regulate the growth of the neuronal structures, and to methods of making and using the same. The present invention relates to methods of identifying compounds which modulate compositions that regulate the growth of neuronal structures.

BACKGROUND OF THE INVENTION

The neuronal cell body is usually round like any other cell. However, these cells have structures, also referred to as "processes", which grow from them to form synaptic connections. Some of these processes carry information away from the cell body; sometimes over very long distances. These long and thin processes are axons. The axon is a thin, static tube. Other processes carry information either towards the cell body, or both towards and away from the cell body. These shorter and usually thicker processes are called dendrites. Both axons and dendrites are called neurites.

During development and the growth stage of neurons, neurites are formed by means of growth cones. A growth cone is the growing tip of a neurite. The growth cone is flattened and highly motile. It is where new material is added and further extension of the axon originates. Controlling where the growth cone crawls controls were the axon will be laid down and thus where it will be present.

The growth cone has several definable parts. The thin, flattened, veil-like processes that stick out and retract from the leading edge are called lamellipodia. The needle-like processes that stick out and retract from the leading edge are called microspikes or filopodia. These are the structures involved in pushing the leading edge of the growth cone forward.

The accurate navigation of growth cones to their appropriate targets requires that they recognize and respond to navigational cues in their immediate environment. Some of these cues encourage extension into certain areas whereas others discourage extension into others. Well characterized molecules that encourage neurite outgrowth in vitro include the extracellular matrix molecule laminin and the neuronal cell surface molecule L1/G4/8D9. These molecules which promote neurite extension are generally widely distributed throughout the body. Laminin immunoreactivity is reasonably widespread in the developing central and peripheral nervous systems. Similarly, L1/G4/8D9 is present on a wide variety of neuronal processes in the developing central nervous system, particularly long projecting axons. It is, therefore, unclear whether the known outgrowth promoting molecules play an important role in self-specific choices growth cones make as they decide between possible routes. Instead, their function is believed to provide a generally permissive environment in which growth cones extend and respond to more specific navigational cues.

Among these more specific cues are molecules that inhibit the motility of particular growth cones. Growth cones have been observed to lose their motile morphology and cease advancing (collapse) on contact with other neurites of different types. Territory formation in vitro may mean the manifestation of a process that leads to selective fasciculation in vivo. Some growth cones have been observed to crawl along specific axonal pathways, or stereotype sequences of axonal pathways in developing embryos. Specific motility inhibiting effects could determine which of several alternative pathways a growth cone will extend on. Growth cones would be expected to prefer growing on axons that do not induce them to collapse while shunning those that do.

It has been observed that, for example, sympathetic growth cones will be inhibited or collapse when coming in contact with retinal neurites. Likewise, growth cones of retinal neurites will collapse when coming in contact with sympathetic neurites. It is believed that such cell activity is achieved through the presence of receptors which specifically respond to specific growth inhibition cues by the molecules which transmit specific cues pertaining to growth. Cues are believed to be present on cell surfaces, particularly on axon surfaces.

When nerve damage occurs, repair is impeded or incapable of occurring due to the failure of neurites to replace damaged axons or dendrites. If an existing neurite is damaged, severed or destroyed, a new neurite is incapable of growing out from the cell body to replace it. The presence of molecules which inhibit neurite growth are believed to be responsible for the difficulty in neurite regeneration.

There is a need for compositions which modulate the activity of molecules which inhibit the growth cone extension. There is a need for a method of identifying molecules which modulate the activity of molecules that inhibit neurite outgrowth. There is a need for a method of treating patients suffering from neuronal damage. There is a need for a method of inducing neurite outgrowth by neutralizing inhibitory molecules.

SUMMARY OF THE INVENTION

One aspect of the present invention relates to essentially pure human collapsin.

One aspect of the present invention relates to an isolated nucleic acid molecule that comprises a nucleotide sequence that is complementary to a nucleotide sequence that encodes a portion of human collapsin.

One aspect of the present invention relates to a method of inhibiting the activity of collapsin by contacting a neuronal cell with nucleic acid molecule that comprises a nucleotide sequence that is complementary to a nucleotide sequence that encodes a portion of human collapsin.

One aspect of the present invention relates to a method of inducing neurite outgrowth by contacting a neuronal cell with nucleic acid molecule that comprises a nucleotide sequence that is complementary to a nucleotide sequence that encodes a portion of human collapsin.

One aspect of the present invention relates to treating an individual suffering from nerve damage comprising the step of contacting a neuronal cell of the individual with nucleic acid molecule that comprises a nucleotide sequence that is complementary to a nucleotide sequence that encodes a portion of human collapsin.

One aspect of the present invention relates to an isolated nucleic acid molecule that comprises a nucleotide sequence that encodes human collapsin.

One aspect of the present invention relates to an expression vector that comprises a nucleotide sequence that encodes human collapsin.

One aspect of the present invention relates to a host cell that comprises an expression vector that comprises a nucleotide sequence that encodes human collapsin.

One aspect of the present invention relates to antibodies which specifically bind to human collapsin.

One aspect of the present invention relates to antibodies which specifically bind to human collapsin and inhibit its activity.

One aspect of the present invention relates to a method of inhibiting the activity of collapsin by contacting a neuronal cell with an antibody that specifically binds to human collapsin.

One aspect of the present invention relates to a method of inducing neurite outgrowth by contacting a neuronal cell with an antibody that specifically binds to human collapsin.

One aspect of the present invention relates to treating an individual suffering from nerve damage comprising the step of contacting a neuronal cell of the individual with an antibody that specifically binds to human collapsin.

One aspect of the present invention relates to a method of identifying compounds that inhibit the activity of human collapsin comprising the steps of contacting a neuronal cell with human collapsin in the presence of a test compound.

DESCRIPTION OF PREFERRED EMBODIMENTS OF THE INVENTION

A growth cone crawls by extending lamellipodia and filopodia forward, attaching them to the surface, and then pulling forward against them. An actively crawling growth cone must be spread on the surface upon which it is growing in order to crawl. The present invention provides a molecule, referred to herein as "collapsin", which stops the crawling by inducing a loss of lamellipodial and filopodial processes. Thus, collapsin inhibits neurite outgrowth. A dramatic change in the growth cone's morphology that is inseparable from the process of advance defines the activity of collapsin.

A partial amino acid sequence for human collapsin is disclosed in SEQ ID NO:1 and SEQ ID NO:2. A partial nucleotide sequence that encodes human collapsin in disclosed in SEQ ID NO:1 and spans from nucleotide 50 to nucleotide 1480.

The present invention relates to essentially pure human collapsin. Additionally, the present invention relates to biologically active fragments thereof. Essentially pure collapsin may be used as a reagent in assays to identify inhibitors of human collapsin. Human collapsin may be isolated from natural sources, produced by recombinant DNA methods or synthesized by standard protein synthesis techniques.

In order to isolate human collapsin from natural sources, samples of natural material may be contacted with antibodies which specifically bind to collapsin. The unbound natural material may be separated from the human collapsin bound to the antibodies. The human collapsin may then be released from the antibodies and purified. Antibodies which bind specifically to human collapsin may be produced by those having ordinary skill in the art with the information provided in SEQ ID NO:1 (i.e. that a portion of human collapsin is encoded by nucleotide 50 to nucleotide 1480 of SEQ ID NO:1) and SEQ ID NO:2 using standard techniques and readily available starting materials. Using such antibodies, one having ordinary skill in the art can produce essentially pure human collapsin form readily available natural sources such as human tissue, particularly discarded human tissue from surgical procedures or human tissue from recently deceased individuals. Preferred human tissue includes tissue associated with neurons such as brain or spinal tissue.

One having ordinary skill in the art can produce human collapsin by recombinant DNA methodology using the information disclosed in SEQ ID NO:1 (i.e. that a portion of human collapsin is encoded by nucleotide 50 to nucleotide 1480 of SEQ ID NO:1) and well known techniques with readily available starting materials. A nucleic acid molecule which comprises a nucleotide sequence encodes human collapsin is inserted into an expression vector which is introduced into a suitable host cell which expresses the nucleotide sequence that encodes human collapsin and produces human collapsin. The human collapsin may be purified by well known methods using readily available starting materials.

A nucleic acid molecule that encodes human collapsin may be isolated from a cDNA library using probes which comprise at least a portion of the nucleotide sequence disclosed in SEQ ID NO:1 between nucleotide 50 and nucleotide 1480 of SEQ ID NO:1. The cDNA library may be generated by well known techniques using neuronal cells which produce collapsin as starting material. cDNA made form whole brain has been used to identify cDNA that encodes collapsin. It is preferred that the cDNA library be generated from human fetal brain cells. A cDNA clone which contains the nucleotide sequence is identified using probes that comprise at least a portion of the nucleotide sequence disclosed in SEQ ID NO:1 between nucleotide 50 and nucleotide 1480 of SEQ ID NO:1. It is preferred that the probes comprise all or most of the nucleotide sequence disclosed in SEQ ID NO:1 between nucleotide 50 and nucleotide 1480 of SEQ ID NO:1 and preferably no other nucleotide sequences. The probes are used to screen the cDNA library using standard hybridization techniques. Alternatively, genomic clones may be isolated using genomic DNA from any human cell as a starting material.

One having ordinary skill in the art can isolate the nucleic acid molecule that encodes human collapsin and insert it into an expression vector using standard techniques and readily available starting materials. One having ordinary skill in the art can, using well known techniques, insert such DNA molecules into a commercially available expression vector for use in well known expression systems. For example, the commercially available plasmid pSE420 (Invitrogen, San Diego, Calif.) may be used for production of collapsin in *E. coli*. The commercially available plasmid pYES2 (Invitrogen, San Diego, Calif.) may, for example, be used for production in *S. cerevisiae* strains of yeast. The commercially available MAXBAC TM complete baculovirus expression system (Invitrogen, San Diego, Calif.) may, for example, be used for production in insect cells. The commercially available plasmid pcDNA I (Invitrogen, San Diego, Calif.) may, for example, be used for production in mammalian cells such as Chinese Hamster Ovary cells. One having ordinary skill in the art can use these commercial expression vectors and systems or others to produce human collapsin or fragments thereof using routine techniques and readily available starting materials. (See e.g., Sambrook et al., *Molecular Cloning a Laboratory Manual*, Second Ed. Cold Spring Harbor Press (1989) which is incorporated herein by reference.) Thus, the desired proteins can be prepared in both prokaryotic and eukaryotic systems, resulting in a spectrum of processed forms of the protein.

The particulars for the construction of expression systems suitable for desired hosts are known to those in the art. Briefly, for recombinant production of the protein, the DNA encoding the polypeptide is suitably ligated into the expression vector of choice. The DNA is operably linked to all regulatory elements which are necessary for expression of the DNA in the selected host. One having ordinary skill in the art can, using well known techniques, prepare expression vectors for recombinant production of the polypeptide.

The expression vector including the DNA that encodes collapsin or a fragment thereof is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate collapsin or fragment that is produced using such expression systems. The methods of purifying human collapsin from natural sources using antibodies which specifically bind to human collapsin as described above, may be equally applied to purifying human collapsin produced by recombinant DNA methodology.

In addition to producing these proteins by recombinant techniques, automated peptide synthesizers may also be employed to produce collapsin or fragments. Such techniques are well known to those having ordinary skill in the art and are useful if derivatives which have substitutions not provided for in DNA-encoded protein production.

The present invention relates to an isolated nucleic acid molecule that comprises a nucleotide sequence that is complementary to a nucleotide sequence that encodes a portion of human collapsin and compositions which contain such nucleic acid molecules. Nucleic acid molecules that comprises a nucleotide sequence that is complementary to a nucleotide sequence that encodes a portion of human collapsin may be used in methods for modulating the activity of RNA that encodes human collapsin. Accordingly nucleic acid molecules that comprises a nucleotide sequence that is complementary to a nucleotide sequence that encodes a portion of human collapsin relate to the field of "antisense" compounds, compounds which are capable of specific hybridization with a nucleotide sequence of an RNA molecule. The antisense compounds of the present invention are useful to inhibit production of collapsin, to induce neurite outgrowth and to treating individuals suffering from nerve damage. The antisense compounds of the present invention are useful in methods of inhibiting production of collapsin, methods of inducing neurite outgrowth and methods of treating individuals suffering from nerve damage. The antisense compounds are useful to regulate gene expression, assaying for RNA and for RNA products through the employment of antisense interactions with such RNA. The antisense compounds of the present invention inhibit the production of human collapsin by interactions with molecules that direct their synthesis, intracellular RNA. By interfering with the production of human collapsin, the inhibitor effect that collapsin has on neurite outgrowth can be modulated and, in the case of individuals suffering from nerve damage, the inhibitory effect of collapsin which suppresses nerve regeneration can be blocked and neurite growth may take place to replace damaged neurites. It is the general object of such therapeutic approaches to interfere with or otherwise modulate gene expression leading to collapsin production.

One method for inhibiting specific gene expression which has been adopted to some degree is the "antisense" approach, where oligonucleotide analogues complimentary to a specific, target, messenger RNA, mRNA sequence are used. A number of workers have reported such attempts. Pertinent reviews include C. A. Stein & J. S. Cohen, *Cancer Research*, vol. 48, pp. 2659–2668 (1988); J. Walder, *Genes & Development*, vol. 2, pp. 502–504 (1988); C. J. Marcus-Sekura, *Anal. Biochemistry*, vol. 172,289–295 (1988); G. Zon, *Journal of Protein Chemistry*, vol. 6, pp-131–145 (1987); G. Zon, *Pharmaceutical Research*, vol. 5, pp. 539–549 (1988); A. R. Van der Krol, J. N. Mol, & A. R. Stuitje, *BioTechniques*, vol. 6, pp. 958–973 (1988) and D. S. Loose-Mitchell, *TIPS*, vol. 9, pp. 45–47 (1988). Each of the foregoing provide background concerning general antisense theory and prior techniques.

Antisense compositions according to the present invention comprise oligonucleotide molecules which are complementary to the nucleotide sequence of the DNA molecule that encodes human collapsin. The oligonucleotides in accordance with this aspect of the invention preferably comprise from about 5 to about 200 nucleotides. The oligonucleotides in accordance with this aspect of the invention more preferably comprise from about 5 to about 50 nucleotides. It is more preferred that such oligonucleotides comprise from about 8 to 25 nucleotides, and still more preferred to have from about 12 to 25 nucleotides.

The oligonucleotides used in accordance with this aspect of the invention may be conveniently and routinely made through the well-known technique of solid phase synthesis using the information provided in SEQ ID NO:I between nucleotide 50 and nucleotide 1480. Equipment for such synthesis is sold by several vendors including Applied Biosystems. Any other means for such synthesis may also be employed, however the actual synthesis of the oligonucleotides are well within the talents of the one having ordinary skill in the art. It is also well known to use similar techniques to prepare other oligonucleotides such as the phosphorothioates and alkylated derivatives.

In accordance with this aspect of the present invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. In preferred embodiments, the oligonucleotide is specifically hybridizable with a transcription initiation site, a translation initiation site, an intron/exon junction or sequences in the 5'- or 3'-untranslated region or 5' cap region.

Oligonucleotides useful in the invention are complementary to the DNA or to the corresponding messenger RNA (mRNA) or pre-messenger RNA. Thus, the oligonucleotides in accordance with the invention preferably have one of the foregoing sequences or an effective portion thereof. Thus, it is preferred to employ any of these oligonucleotides as set forth above or any of the similar nucleotides which persons of ordinary skill in the art can prepare from knowledge of the preferred antisense targets for the modulation of collapsin production.

Oligonucleotides may be formulated in a pharmaceutical composition, which may include carriers, thickeners, diluents, buffers, preservatives, surface active agents and the like in addition to the oligonucleotide. Pharmaceutical compositions may also include one or more active ingredients such as antimicrobial agents, antiinflammatory agents, anesthetics, and the like in addition to oligonucleotide.

The pharmaceutical composition may be administered in a number of ways. It is preferred that the compositions are administered locally at or near the site where nerve damage has occurred. It is preferred that the administration of compositions be by way of a nerve cuff. Those having ordinary skill in the art can readily isolate the nerve cell and provide a nerve cuff which allows directed administration to the nerve cell. Since regeneration can take weeks or months, it may be necessary to deliver therapeutic compounds over a long period of time. The formulation of therapeutic compounds within a polymer matrix which is implanted provides slow release of the therapeutic agent. Alternatively, slow release of a therapeutic compound may be achieved using an implanted osmotic mini-pump. Drug delivery systems can be designed by those having ordinary skill in the art (see: "Treatise on controlled drug delivery" 1992 Agis Kydonieus, ed. Marcel Dekker, NY, N.Y., which is incorporated herein by reference).

Dosing is dependent on severity and responsiveness of nerve to induction of neurite outgrowth. Treatment lasting from several days to several months or until neurite outgrowth is complete is contemplated. Persons of ordinary skill can determine a therapeutically effective amount and optimum dosages, dosing methodologies and repetition rates.

The present invention relates to antibodies which specifically bind to human collapsin. Antibodies which bind specifically to human collapsin may be produced by those having ordinary skill in the art with the information provided in SEQ ID NO:1 and SEQ ID NO:2 using standard techniques and readily available starting materials. As disclosed above, such antibodies may be used to purify human collapsin from natural sources or from material present when producing human collapsin by recombinant DNA methodology. Additionally, such antibodies are useful to inhibit the activity of collapsin by contacting a neuronal cell with an antibody that specifically binds to human collapsin, to induce neurite outgrowth by contacting a neuronal cell with an antibody that specifically binds to human collapsin and to treat an individual suffering from nerve damage comprising the step of contacting a neuronal cell of the individual with an antibody that specifically binds to human collapsin. Accordingly, such antibodies are useful in methods of inhibiting the activity of collapsin comprising contacting a neuronal cell with an antibody that specifically binds to human collapsin, methods of inducing neurite outgrowth comprising contacting a neuronal cell with an antibody that specifically binds to human collapsin and of treating an individual suffering from nerve damage comprising the step of contacting a neuronal cell of the individual with an antibody that specifically binds to human collapsin.

As used herein, the term "antibody" is meant to refer to complete, intact antibodies, Fab fragments, and F(ab)$_2$ fragments. It is preferred that antibodies be complete, intact antibodies. The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) *ANTIBODIES: A Laboratory Manual*, Cold Spring Harbor Laboratory, Cold Spring Harbor, N.Y.

Pharmaceutical compositions comprising antibodies may be formulated by one having ordinary skill in the art with compositions selected depending upon the chosen mode of administration. Suitable pharmaceutical carriers are described in *Remington's Pharmaceutical Sciences*, A. Osol, a standard reference text in this field, which is incorporated herein by reference.

The pharmaceutical compositions of the present invention may be administered to an individual suffering from nerve damage in order to inactivate collapsin present at and near the site of nerve damage so that neurite outgrowth can be induced and replacement of damaged neurites can occur.

As used herein, the term "effective amount of antibodies" is meant to refer to the amount of an antibodies which is sufficient to inactivate collapsin and induce neurite outgrowth. Effective amount can be readily determined by routine experimentation.

The present invention relates to methods of identifying compounds that inhibit the activity of human collapsin comprising the steps of contacting a neuronal cell with human collapsin in the presence of a test compound.

In some embodiments of the present invention an assay identifying compounds which inhibit the growth cone collapsing activity of human collapsin is provided. In some embodiments, explanted embryonic day (E7) dorsal root ganglia (DRGs) are used as test cells. Other cells that can be cultured and that display neurite outgrowth include sympathetic, ciliary, diencephalic, and superior collicular neurons as well as spinal or brainstem motoneurons. DRGs extend long neurites on laminin-coated glass. Under normal culture conditions, the tips of nearly all neurites have well-defined growth cones as judged by the presence of lamellipodia and filopodia (FIG. 1). Addition of human collapsin to DRGs that are on laminin-coated glass induces the collapse of DRG growth cones. A growth cone is considered collapsed if it has no observable lamellipodia and no more than two filopodia.

According to the present invention, compounds are identified which modulate the ability of human collapsin to collapse a growth cone. A screen has been designed which compares the ability of human collapsin to collapse a growth cone of a cell in the presence or absence of a test compound. Using this screen, compounds can be identified which modulate collapsin activity. In particular, compounds can be identified which either inhibit collapsin's inhibitory activity. Such compounds may be useful to promote neurite outgrowth.

According to the present invention, a test assay is run wherein cells are maintained on a substrate that is permissive for induction of growth cones. Two basic requirements are required for optimal outgrowth: an appropriate culture medium and substratum that permits outgrowth. The addition of additional fibroblast growth factor (FGF) can improve outgrowth. Laminin is an appropriate substratum for the growth of all peripheral and some central axons, whereas G4/L1 works better for most central axons. Other substrata include fibronectin, thrombospondin, N-cadherin, poly-lysine, polyornathine, or cell lines transfected with adhesion molecules. The most important factors in neural cultures are the base medium, glutamine supplement, added growth factors, serum, and the substratum. Serum is not required; NGF and growth factors in the pituitary extract take its place. Substrates permissive for induction of DRG growth cones include a solid phase comprising compounds known to induce neurite outgrowth such as the extracellular matrix molecule laminin or the neuronal cell surface molecule L1/G4/8D9. In some embodiments, the permissive substrate is a laminin-coated glass plates. A DRG cell placed on a permissive substrate such as laminin-coated glass plates form visible growth cones. Clumps of neurons are explanted and axons grow out of the clumps. In 6–12 hours minimum, the axons can be observed to be well away from the clump. It is preferred to perform the assay after approximately 18 hours in culture. It is preferred not to perform the assay after 24 hours as the growth cones are more variable in appearance and are harder to score. Collapsin and test compound are then added. Collapsin is added at a concentration of between 1 pM-500 mM. It is preferred that the amount of collapsin added is in the concentration of about 10 pM to about 200 pM, more preferably from about 10 pM to about 100 pM, most preferably about 10 pM. In some embodiments, a monoclonal antibody that inhibits collapsin activity is added in a range of between about 0.1 µg/ml to about 1 mg/ml, preferably 1 µg/ml to about 100 µg/ml, preferably about 10 µg/ml. In some embodiments, a peptide that inhibits collapsin activity is added in a range of between about 0.01 mg/ml to about 100 mg/ml, preferably about 0.1 mg/ml to about 10 mg/ml, more preferably about 1 mg/ml. Synthetic chemicals may be added in some embodiments in the range of about 0.1 ng/ml to about 100 ng/ml. In such embodiments, it is preferred that the compound is added to a concentration of about 10 ng/ml. In some embodiments of the invention, the preferred concentration of test compound is between 1 µM and 500 µM. A preferred concentration is 10 mM to 100 mM. In some preferred embodiments, it is desirable to use a series of dilutions of test compounds. The collapsing factor acts within 5 minutes and the growth cones remain collapsed for hours. The cells are fixed within 0.25–6 hours, preferably 1 hour after addition of collapsin and test compound. The collapse of the growth cone is then scored. A growth cone is considered collapsed if it has no observable lamellipodia and no more than two filopodia. If a control assay is run, it is identical to the test assay except no test compound is added. In the control assay, human collapsin is contacted with the DRG in the absence of the test compound. The collapse of the growth cone is scored. As an additional control, an assay identical to the test assay is run except instead of a test compound of unknown activity, a known inhibitor of human collapsin is added. An example of a known inhibitor is an antibody that specifically binds to human collapsin. In such a control assay, human collapsin and antibodies that specifically binds to human collapsin are contacted with the DRG. The collapse of the growth cone is scored. Using proper controls, the activity of a collapsin inhibitor can be confirmed. The following data indicates a test compound is inhibiting collapsin activity.

| | |
|---|---|
| 1) without collapsin or test compound | no collapse |
| 2) with collapsin only | collapse |
| 3) with test compound only | no collapse |
| 4) with collapsin and test compound | no collapse |

DRGs may be obtained by removing them from E7 White Leghorn chick embryos, cut into halves or quarters, and explanted onto laminin-coated glass coverslips on F12 medium including nerve growth factor, fetal calf serum, chick serum, and other supplements as described in Kapfhammer et al. (1986). Experiments are performed 10–48 hours later; preferably 20–30 hours later.

For some experiments, DRG explants are grown in immunopurified G4 (Lagenaur and Lemmon 1987). Glass coverslips are first dipped in a solution of Schleicher and Schuell BA83 nitrocellulose dissolved in methanol, the methanol is allowed to dry, and 20 µl of G4 suspended in Hank's solution containing 0.1% deoxycholate is absorbed to the coverslip for 5 min. The coverslip is then soaked in a 3 mg/ml solution of hemoglobin for 30 min to block proteins from binding to the nitrocellulose from the culture medium. The coverslips are used after removing the hemoglobin with several rinses of Hank's solution.

Before testing for collapsing activity, human collapsin can be purified. Preferably it is dialyzed against PBS for 12–18 hr and then against F12 medium without additives for a minimum of 4 hr.

DRGs are cultured on 9 or 10 mm glass coverslips coated with laminin (Kapfhammer et al., 1986) and isolated from one another in the wells of a standard 48 well microplate. Human collapsin (50 ul or less dialysate per 500 ul of medium) and a solution comprising test compound are added to the medium in the well and gently mixed once or twice by pipetting approximately one-half of the contents of the well in and out of the well. The cultures are incubated at 37° C. and 5% $CO_2$ for 60 min before fixing them with 4% paraformaldehyde in PBS containing 10% sucrose.

Fixed preparations are scored qualitatively or quantitatively. In cultures not exposed to human collapsin or exposed to human collapsin and a known inhibitor, nearly all should have extending neurites possessing recognizable growth cones at their tips. These have flattened lamellipodia and/or clusters of filopodia that are easily visualized in phase-contrast microscopy. In contrast, the tips of neurites exposed to human collapsin only are bullet-shaped and have no lamellipodia or filopodia. The growth cones of cultures exposed to human collapsin and a test compound are scored. If the DRGs in the test assay have extending neurites possessing recognizable growth cones at their tips, the test compound may be an inhibitor of human collapsin. Tips of neurites that are bullet-shaped and have no lamellipodia or filopodia indicate that the test compound is not an inhibitor.

EXAMPLE 1

Materials

DRGs were removed from E7 White Leghorn chick embryos, cut into halves or quarters, and explanted onto laminin-coated glass coverslips on F12 medium including nerve growth factor, fetal calf serum, chick serum, and other supplements as described in Kapfhammer et al. (1986). Small bits of E6 retinal tissue were explanted similarly. All experiments were performed 20–30 hr later. Growth cones are less well spread and more difficult to score when older cultures are used.

For some experiments, DRG explants were grown in immunopurified G4 (Lagenaur and Lemmon 1987). Glass coverslips were first dipped in a solution of Schleicher and Schuell BA83 nitrocellulose dissolved in methanol, the methanol was allowed to dry, and 20 µl of G4 suspended in Hank's solution containing 0.1% deoxycholate was absorbed to the coverslip for 5 min. The coverslip was then soaked in a 3 mg/ml solution of hemoglobin for 30 min to block proteins from binding to the nitrocellulose from the culture medium. The coverslips were used after removing the hemoglobin with several rinses of Hank's solution.

Before testing for collapsing activity, human collapsin is dialyzed against PBS for 12–18 hr and then against F12 medium without additives for a minimum of 4 hr.

DRGs were cultured on 9 or 10 mm glass coverslips coated with laminin (Kapfhammer et al., 1986) and isolated from one another in the wells of a standard 48 well microplate. Test dialysates (50 ul or less dialysate per 500 ul of medium) were added to the medium in the well and gently mixed once or twice by pipetting approximately one-half of the contents of the well in and out of the well. The cultures were incubated at 37° C. and 5% CO$_2$ for 60 min before fixing them with 4% paraformaldehyde in PBS containing 10% sucrose.

Fixed preparations could be scored qualitatively or quantitatively. In untreated cultures, nearly all extending neurites possess recognizable growth cones at their tips. These have flattened lamellipodia and/or clusters of filopodia that are easily visualized in phase-contrast microscopy. In contrast, the tips of neurites exposed to strong collapsing activity are bullet-shaped and have no lamellipodia or filopodia. Intermediate conditions can be characterized by the percentage of neurite tips without lamellipodia or filopodia. Only single, uncrowded neurite tips are scored.

---

We claim:

1. An antibody capable of specifically binding to a protein that comprises at least a portion of SEQ ID NO:2.

2. The antibody of claim 1 capable of specifically binding to a protein comprising at least a portion of SEQ ID NO:2 which comprises amino acids 9 to 19 of SEQ ID NO:2.

3. The antibody of claim 1 capable of specifically binding to a protein comprising at least a portion of SEQ ID NO:2 which comprises amino acids 51 to 65 of SEQ ID NO:2.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1481 base pairs
        ( B ) TYPE: nucleic acid
        ( C ) STRANDEDNESS: double
        ( D ) TOPOLOGY: both ( i i ) MOLECULE TYPE: cDNA ( i x ) FEATURE:
        ( A ) NAME/KEY: CDS
        ( B ) LOCATION: 50..1480

( x i ) SEQUENCE DESCRIPTION: SEQ ID NO:1:

```
CGGAGCAAGG AACAGGTTAT TTTAGGTTAT AAAAATTTAA TACAGAATA CTT GAA              55
                                                       Leu Glu
                                                         1

CAT GAC AAT CCT GAA GAT GAC AAA GTA TAC TTT TTC TTC CGT GAA AAT          103
His Asp Asn Pro Glu Asp Asp Lys Val Tyr Phe Phe Phe Arg Glu Asn
          5               10                  15

GCA ATA GAT GGA GAA CAC TCT GGA AAA GCT ACT CAC GCT AGA ATA GGT          151
Ala Ile Asp Gly Glu His Ser Gly Lys Ala Thr His Ala Arg Ile Gly
     20                  25                  30

CAG ATA TGC AAG AAT GAC TTT GGA GGG CAC AGA AGT CTG GTG AAT AAA          199
Gln Ile Cys Lys Asn Asp Phe Gly Gly His Arg Ser Leu Val Asn Lys
 35                  40                  45                  50

TGG ACA ACA TTC CTC AAA GCT CGT CTG ATT TGC TCA GTG CCA GGT CCA          247
Trp Thr Thr Phe Leu Lys Ala Arg Leu Ile Cys Ser Val Pro Gly Pro
                 55                  60                  65

AAT GGC ATT GAC ACT CAT TTT GAT GAA CTG CAG GAT GTA TTC CTA ATG          295
Asn Gly Ile Asp Thr His Phe Asp Glu Leu Gln Asp Val Phe Leu Met
             70                  75                  80

AAC TTT AAA GAT CCT AAA AAT CCA GTT GTA TAT GGA GTG TTT ACG ACT          343
Asn Phe Lys Asp Pro Lys Asn Pro Val Val Tyr Gly Val Phe Thr Thr
         85                  90                  95
```

```
TCC AGT AAC ATT TTC AAG GGA TCA GCC GTG TGT ATG TAT AGC ATG AGT      391
Ser Ser Asn Ile Phe Lys Gly Ser Ala Val Cys Met Tyr Ser Met Ser
    100             105             110

GAT GTG AGA AGG GTG TTC CTT GGT CCA TAT GCC CAC AGG GAT GGA CCC      439
Asp Val Arg Arg Val Phe Leu Gly Pro Tyr Ala His Arg Asp Gly Pro
115             120             125             130

AAC TAT CAA TGG GTG CCT TAT CAA GGA AGA GTC CCC TAT CCA CGG CCA      487
Asn Tyr Gln Trp Val Pro Tyr Gln Gly Arg Val Pro Tyr Pro Arg Pro
                135             140             145

GGA ACT TGT CCC AGC AAA ACA TTT GGT GGT TTT GAC TCT ACA AAG GAC      535
Gly Thr Cys Pro Ser Lys Thr Phe Gly Gly Phe Asp Ser Thr Lys Asp
            150             155             160

CTT CCT GAT GAT GTT ATA ACC TTT GCA AGA AGT CAT CCA GCC ATG TAC      583
Leu Pro Asp Asp Val Ile Thr Phe Ala Arg Ser His Pro Ala Met Tyr
        165             170             175

AAT CCA GTG TTT CCT ATG AAC AAT CGC CCA ATA GTG ATC AAA ACG GAT      631
Asn Pro Val Phe Pro Met Asn Asn Arg Pro Ile Val Ile Lys Thr Asp
    180             185             190

GTA AAT TAT CAA TTT ACA CAA ATC GTC GTA GAC CGA GTG GAT GCA GAA      679
Val Asn Tyr Gln Phe Thr Gln Ile Val Val Asp Arg Val Asp Ala Glu
195             200             205             210

GAT GGA CAG TAT GAT GTT ATG TTT ATC GGA ACA GAT GTT GGG ACC GTT      727
Asp Gly Gln Tyr Asp Val Met Phe Ile Gly Thr Asp Val Gly Thr Val
                215             220             225

CTT AAA GTA GTT TCA ATT CCT AAG GAG ACT TGG TAT GAT TTA GAA GAG      775
Leu Lys Val Val Ser Ile Pro Lys Glu Thr Trp Tyr Asp Leu Glu Glu
            230             235             240

GTT CTG CTG GAA GAA ATG ACA GTT TTT CGG GAA CCG ACT GCT ATT TCA      823
Val Leu Leu Glu Glu Met Thr Val Phe Arg Glu Pro Thr Ala Ile Ser
        245             250             255

GCA ATG GAG CTT TCC ACT AAG CAG CAA CAA CTA TAT ATT GGT TCA ACG      871
Ala Met Glu Leu Ser Thr Lys Gln Gln Gln Leu Tyr Ile Gly Ser Thr
    260             265             270

GCT GGG GTT GCC CAG CTC CCT TTA CAC CGG TGT GAT ATT TAC GGG AAA      919
Ala Gly Val Ala Gln Leu Pro Leu His Arg Cys Asp Ile Tyr Gly Lys
275             280             285             290

GCG TGT GCT GAG TGT TGC CTC GCC CGA GAC CCT TAC TGT GCT TGG GAT      967
Ala Cys Ala Glu Cys Cys Leu Ala Arg Asp Pro Tyr Cys Ala Trp Asp
                295             300             305

GGT TCT GCA TGT TCT CGC TAT TTT CCC ACT GCA AAG AGA CGC ACA AGA     1015
Gly Ser Ala Cys Ser Arg Tyr Phe Pro Thr Ala Lys Arg Arg Thr Arg
            310             315             320

CGA CAA GAT ATA AGA AAT GGA GAC CCA CTG ACT CAC TGT TCA GAC TTA     1063
Arg Gln Asp Ile Arg Asn Gly Asp Pro Leu Thr His Cys Ser Asp Leu
        325             330             335

CAC CAT GAT AAT CAC CAT GGC CAC AGC CCT GAA GAG AGA ATC ATC TAT     1111
His His Asp Asn His His Gly His Ser Pro Glu Glu Arg Ile Ile Tyr
    340             345             350

GGT GTA GAG AAT AGT AGC ACA TTT TTG GAA TGC AGT CCG AAG TCG CAG     1159
Gly Val Glu Asn Ser Ser Thr Phe Leu Glu Cys Ser Pro Lys Ser Gln
355             360             365             370

AGA GCG CTG GTC TAT TGG CAA TTC CAG AGG CGA AAT GAA GAG CGA AAA     1207
Arg Ala Leu Val Tyr Trp Gln Phe Gln Arg Arg Asn Glu Glu Arg Lys
                375             380             385

GAA GAG ATC AGA GTG GAT GAT CAT ATC ATC AGG ACA GAT CAA GGC CTT     1255
Glu Glu Ile Arg Val Asp Asp His Ile Ile Arg Thr Asp Gln Gly Leu
            390             395             400

CTG CTA CGT AGT CTA CAA CAG AAG GAT TCA GGC AAT TAC CTC TGC CAT     1303
Leu Leu Arg Ser Leu Gln Gln Lys Asp Ser Gly Asn Tyr Leu Cys His
        405             410             415

GCG GTG GAA CAT GGG TTC ATA CAA ACT CTT CTT AAG GTA ACC CTG GAA     1351
```

-continued

| | | | | | | | | | | | | | | | |
|---|---|---|---|---|---|---|---|---|---|---|---|---|---|---|---|
|Ala|Val 420|Glu|His|Gly|Phe|Ile 425|Gln|Thr|Leu|Leu|Lys 430|Val|Thr|Leu|Glu|

| | | | | | | | | | | | | | | | | |
|---|---|---|---|---|---|---|---|---|---|---|---|---|---|---|---|---|
|GTC|ATT|GAC|AAC|GAG|CAT|TTG|GAA|GAA|CTT|CTT|CAT|AAA|GAT|GAT|GAT|1399|
|Val 435|Ile|Asp|Asn|Glu 440|His|Leu|Glu|Glu|Leu|Leu 445|His|Lys|Asp|Asp|Asp 450| |

| | | | | | | | | | | | | | | |
|---|---|---|---|---|---|---|---|---|---|---|---|---|---|---|
|GGA|CAT|GGC|TCT|AAG|ACC|AAA|GAA|ATG|TCC|AAT|AGC|ATG|ACA|CCT|AGC|1447|
|Gly|His|Gly|Ser|Lys 455|Thr|Lys|Glu|Met|Ser 460|Asn|Ser|Met|Thr|Pro 465|Ser|

| | | | | | | | | |
|---|---|---|---|---|---|---|---|---|
|CAG|AAG|GTC|TGG|TAC|AGA|GAC|TTC|ATG|CAG|CCC|G|1481|
|Gln|Lys|Val|Trp 470|Tyr|Arg|Asp|Phe|Met 475|Gln|Pro| |

(2) INFORMATION FOR SEQ ID NO:2:

(i) SEQUENCE CHARACTERISTICS:
        (A) LENGTH: 477 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | | |
|---|---|---|---|---|---|---|---|---|---|---|---|---|---|---|---|
|Leu 1|Glu|His|Asp|Asn 5|Pro|Glu|Asp|Asp|Lys 10|Val|Tyr|Phe|Phe|Phe 15|Arg|
|Glu|Asn|Ala|Ile 20|Asp|Gly|Glu|His|Ser 25|Gly|Lys|Ala|Thr|His 30|Ala|Arg|
|Ile|Gly|Gln 35|Ile|Cys|Lys|Asn|Asp 40|Phe|Gly|Gly|His|Arg 45|Ser|Leu|Val|
|Asn|Lys 50|Trp|Thr|Thr|Phe|Leu 55|Lys|Ala|Arg|Leu|Ile 60|Cys|Ser|Val|Pro|
|Gly 65|Pro|Asn|Gly|Ile|Asp 70|Thr|His|Phe|Asp|Glu 75|Leu|Gln|Asp|Val|Phe 80|
|Leu|Met|Asn|Phe|Lys 85|Asp|Pro|Lys|Asn|Pro 90|Val|Val|Tyr|Gly|Val 95|Phe|
|Thr|Thr|Ser|Ser 100|Asn|Ile|Phe|Lys|Gly 105|Ser|Ala|Val|Cys|Met 110|Tyr|Ser|
|Met|Ser|Asp 115|Val|Arg|Arg|Val|Phe 120|Leu|Gly|Pro|Tyr|Ala 125|His|Arg|Asp|
|Gly|Pro|Asn 130|Tyr|Gln|Trp|Val|Pro 135|Tyr|Gln|Gly|Arg|Val 140|Pro|Tyr|Pro|
|Arg 145|Pro|Gly|Thr|Cys|Pro 150|Ser|Lys|Thr|Phe|Gly 155|Gly|Phe|Asp|Ser|Thr 160|
|Lys|Asp|Leu|Pro|Asp 165|Asp|Val|Ile|Thr|Phe 170|Ala|Arg|Ser|His|Pro 175|Ala|
|Met|Tyr|Asn|Pro 180|Val|Phe|Pro|Met|Asn 185|Asn|Arg|Pro|Ile|Val 190|Ile|Lys|
|Thr|Asp|Val 195|Asn|Tyr|Gln|Phe|Thr 200|Gln|Ile|Val|Val|Asp 205|Arg|Val|Asp|
|Ala|Glu 210|Asp|Gly|Gln|Tyr|Asp 215|Val|Met|Phe|Ile|Gly 220|Thr|Asp|Val|Gly|
|Thr 225|Val|Leu|Lys|Val|Val 230|Ser|Ile|Pro|Lys|Glu 235|Thr|Trp|Tyr|Asp|Leu 240|
|Glu|Glu|Val|Leu|Leu 245|Glu|Glu|Met|Thr|Val 250|Phe|Arg|Glu|Pro|Thr 255|Ala|
|Ile|Ser|Ala|Met 260|Glu|Leu|Ser|Thr|Lys 265|Gln|Gln|Gln|Leu|Tyr 270|Ile|Gly|
|Ser|Thr|Ala 275|Gly|Val|Ala|Gln|Leu 280|Pro|Leu|His|Arg|Cys 285|Asp|Ile|Tyr|
|Gly|Lys|Ala|Cys|Ala|Glu|Cys|Cys|Leu|Ala|Arg|Asp|Pro|Tyr|Cys|Ala|

|     | 290 |     |     |     | 295 |     |     |     | 300 |     |     |     |     |
| --- | --- | --- | --- | --- | --- | --- | --- | --- | --- | --- | --- | --- | --- |
| Trp 305 | Asp | Gly | Ser | Ala | Cys 310 | Ser | Arg | Tyr | Phe | Pro 315 | Thr | Ala | Lys | Arg | Arg 320 |
| Thr | Arg | Arg | Gln | Asp 325 | Ile | Arg | Asn | Gly | Asp 330 | Pro | Leu | Thr | His | Cys 335 | Ser |
| Asp | Leu | His | His 340 | Asp | Asn | His | His | Gly 345 | His | Ser | Pro | Glu | Glu 350 | Arg | Ile |
| Ile | Tyr | Gly 355 | Val | Glu | Asn | Ser | Ser 360 | Thr | Phe | Leu | Glu | Cys 365 | Ser | Pro | Lys |
| Ser | Gln 370 | Arg | Ala | Leu | Val | Tyr 375 | Trp | Gln | Phe | Gln | Arg 380 | Arg | Asn | Glu | Glu |
| Arg 385 | Lys | Glu | Glu | Ile | Arg 390 | Val | Asp | Asp | His | Ile 395 | Ile | Arg | Thr | Asp | Gln 400 |
| Gly | Leu | Leu | Leu | Arg 405 | Ser | Leu | Gln | Gln | Lys 410 | Asp | Ser | Gly | Asn | Tyr 415 | Leu |
| Cys | His | Ala | Val 420 | Glu | His | Gly | Phe | Ile 425 | Gln | Thr | Leu | Leu | Lys 430 | Val | Thr |
| Leu | Glu | Val 435 | Ile | Asp | Asn | Glu | His 440 | Leu | Glu | Glu | Leu | Leu 445 | His | Lys | Asp |
| Asp 450 | Asp | Gly | His | Gly | Ser | Lys 455 | Thr | Lys | Glu | Met | Ser 460 | Asn | Ser | Met | Thr |
| Pro 465 | Ser | Gln | Lys | Val | Trp 470 | Tyr | Arg | Asp | Phe | Met 475 | Gln | Pro |     |     |     |